(12) United States Patent
Farrow

(10) Patent No.: US 10,596,764 B2
(45) Date of Patent: Mar. 24, 2020

(54) LYMPHATIC CHANNELING MEDICAL GARMENT

(71) Applicant: Farrow Innovations LLC, Bryan, TX (US)

(72) Inventor: Wade P. Farrow, College Station, TX (US)

(73) Assignee: Farrow Innovations LLC, Bryan, TX (US)

( * ) Notice: Subject to any disclaimer, the term of this patent is extended or adjusted under 35 U.S.C. 154(b) by 1018 days.

(21) Appl. No.: 15/095,688

(22) Filed: Apr. 11, 2016

(65) Prior Publication Data

US 2016/0310348 A1    Oct. 27, 2016

Related U.S. Application Data

(60) Provisional application No. 62/153,499, filed on Apr. 27, 2015.

(51) Int. Cl.
| | | |
|---|---|---|
| *A61F 13/06* | (2006.01) | |
| *B29C 65/02* | (2006.01) | |
| *A61F 13/08* | (2006.01) | |
| *B29C 65/48* | (2006.01) | |

(52) U.S. Cl.
CPC .............. *B29C 65/02* (2013.01); *A61F 13/06* (2013.01); *A61F 13/08* (2013.01); *B29C 65/48* (2013.01)

(58) Field of Classification Search
CPC ............ A61H 23/0218; A61H 23/0263; A61H 23/04; A61H 2205/04; A61H 9/0021; A61H 2201/5007; A61H 9/0078; A61G 15/002; A61G 1/04; A61F 5/0585; A61F 5/0111; A61F 5/0118; A61F 5/01; A61F 5/05833; A61F 5/05841; A61F 13/06; A61F 13/08; B29C 65/02

See application file for complete search history.

(56) References Cited

U.S. PATENT DOCUMENTS

| | | | | |
|---|---|---|---|---|
| 3,983,870 | A | * | 10/1976 | Herbert .................. A41B 11/12 602/63 |
| 4,068,318 | A | * | 1/1978 | McMahon ............. A41D 20/00 2/170 |
| 4,832,010 | A | | 5/1989 | Lerman |
| 2003/0213269 | A1 | | 11/2003 | Peeler et al. |
| 2005/0113729 | A1 | | 5/2005 | Scott et al. |
| 2005/0192524 | A1 | | 9/2005 | Lipshaw et al. |

(Continued)

FOREIGN PATENT DOCUMENTS

WO        2010025186 A1      3/2010

OTHER PUBLICATIONS

Extended European Search Report for EP Application No. 16786907.2 dated Nov. 14, 2018; 13 pages.

(Continued)

*Primary Examiner* — Ophelia A Hawthorne

(74) *Attorney, Agent, or Firm* — Shumaker, Loop & Kendrick, LLP

(57) ABSTRACT

A medical garment for channeling edema from a body region, that include at least one stretchable fabric substrate and multiple, separate elements secured to the at least one stretchable fabric substrate with substantially uniform spacing between the elements in a first zone such that the elements extend substantially parallel to one another in the first zone.

9 Claims, 13 Drawing Sheets

(56) References Cited

U.S. PATENT DOCUMENTS

| | | | |
|---|---|---|---|
| 2008/0269654 A1 | 10/2008 | Chardon-Bras et al. | |
| 2010/0312160 A1 | 12/2010 | Creighton et al. | |
| 2013/0191977 A1* | 8/2013 | Mayeri | A41D 13/1245 |
| | | | 2/455 |
| 2015/0032039 A1* | 1/2015 | Farrow | A61H 9/005 |
| | | | 601/84 |

OTHER PUBLICATIONS

International Search Report and Written Opinion of corresponding International Application No. PCT/US2016/026921 dated Jul. 26, 2016 (8 pages).

* cited by examiner

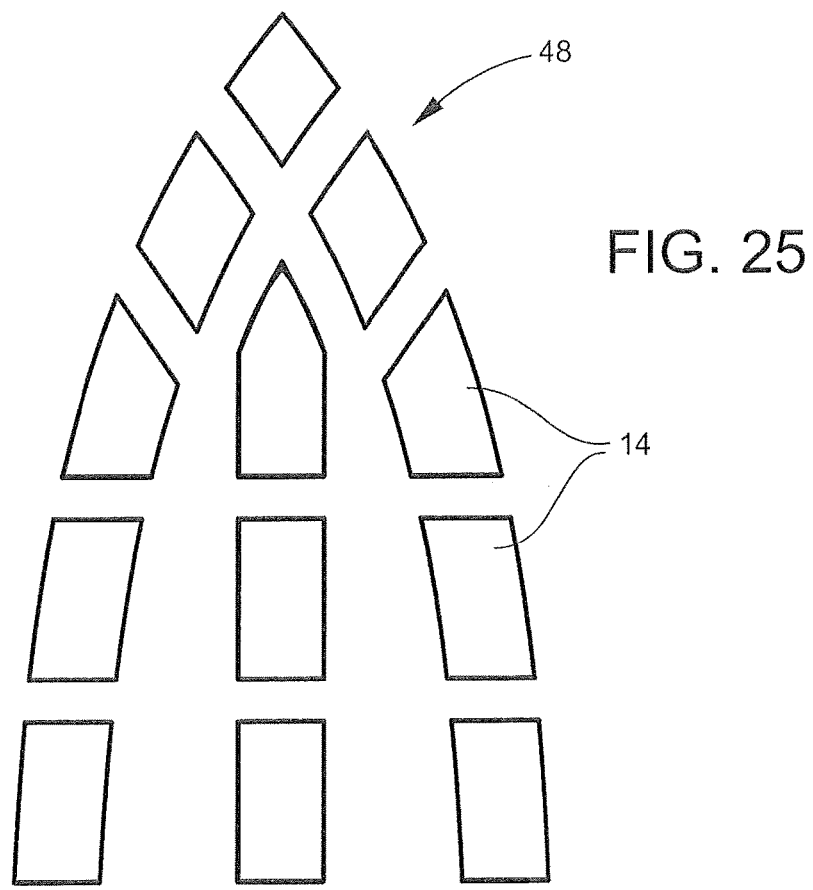
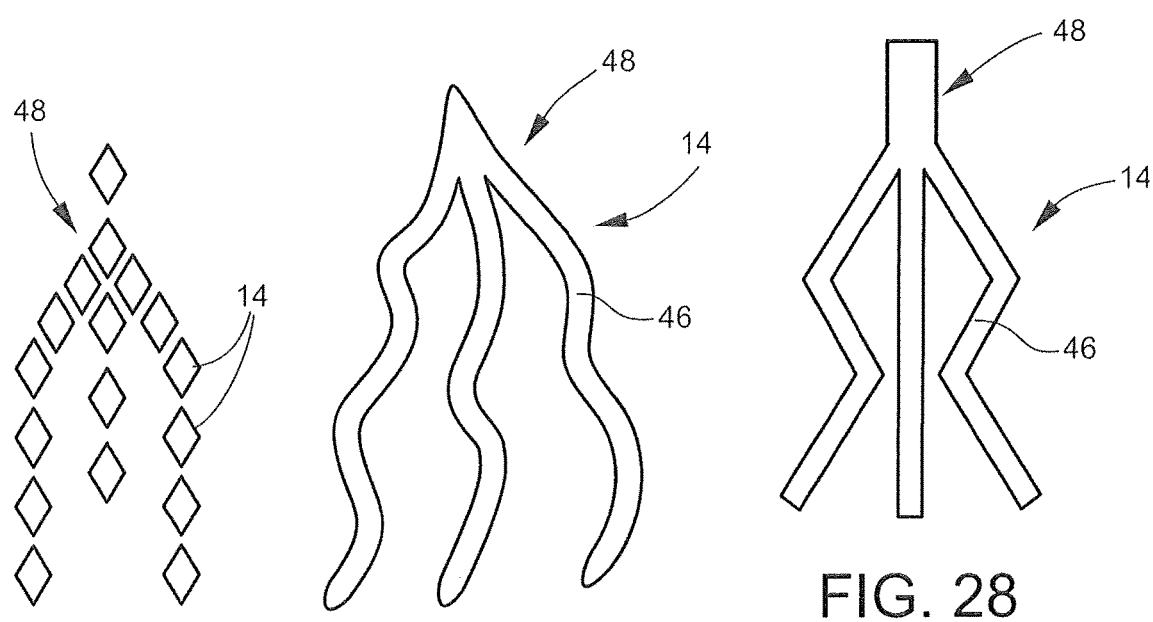
FIG. 25
FIG. 26  FIG. 27  FIG. 28

LYMPHATIC CHANNELING MEDICAL GARMENT

CROSS REFERENCE TO RELATED APPLICATION

This application claims priority to and benefit from U.S. Provisional Application No. 62/153,499, filed on Apr. 27, 2015, the entire contents of which are expressly incorporated herein by reference.

FIELD OF THE INVENTION

This disclosure relates to apparatus, methods, and systems for treating medical conditions by channeling lymphatic flow of a human or animal body.

BACKGROUND OF THE INVENTION

Excessive interstitial fluid accumulation, referred to as edema, may arise from a variety of illnesses and conditions, including trauma, post-surgical recovery, a medicated conduction, congestive heart failure, renal insufficiency, venous valvular insufficiency, postphlebotic syndrome, and lymphedema. Compression methods and systems control edema by reducing interstitial fluid. This in turn may increase nutrient delivery to tissues, remove waste from tissues, relieve pain from swelling, increase tissue oxygenation, promote wound healing, and decrease risk of infection. However, typical compression technologies have certain drawbacks.

For example, many compression garments are bulky, heavy to lift, and do not breathe well. This can make them uncomfortable to wear. Padded garments are also often expensive to the patient. Additional, many compression garments do not fully leverage the lymphatic system of the patient in the treatments applied to that patient. Accordingly, what is needed is an improved system for treating patient with edema.

BRIEF DESCRIPTION OF THE DRAWINGS

The foregoing features of the present invention will become more fully apparent from the following description, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

FIG. 20 is a schematic diagram illustrating one embodiment of a system applied to a breast or chest area, the system including multiple elements that are anatomical in accordance with the present invention and may be used to reduce chest wall or breast lymphedema, reduce swelling from breast biopsy, reduction, or lumpectomy or other surgical treatments, or the like;

FIG. 21 is a schematic diagram illustrating another embodiment of a system applied to a breast or chest area, the system including an element that is anatomical in accordance with the present invention and may be used to reduce chest wall or breast lymphedema, reduce swelling from breast biopsy, reduction, or lumpectomy or other surgical treatments, or the like;

FIG. 25 is a schematic diagram illustrating a plan view of another alternative embodiment of an element that is anatomical in accordance with the present invention;

FIG. 26 is a schematic diagram illustrating a plan view of another alternative embodiment of an element that is anatomical in accordance with the present invention;

FIG. 27 is a schematic diagram illustrating a plan view of another alternative embodiment of an element that is anatomical in accordance with the present invention;

FIG. 28 is a schematic diagram illustrating a plan view of another alternative embodiment of an element that is anatomical in accordance with the present invention.

DETAILED DESCRIPTION OF SELECTED EMBODIMENTS

Figure 1:
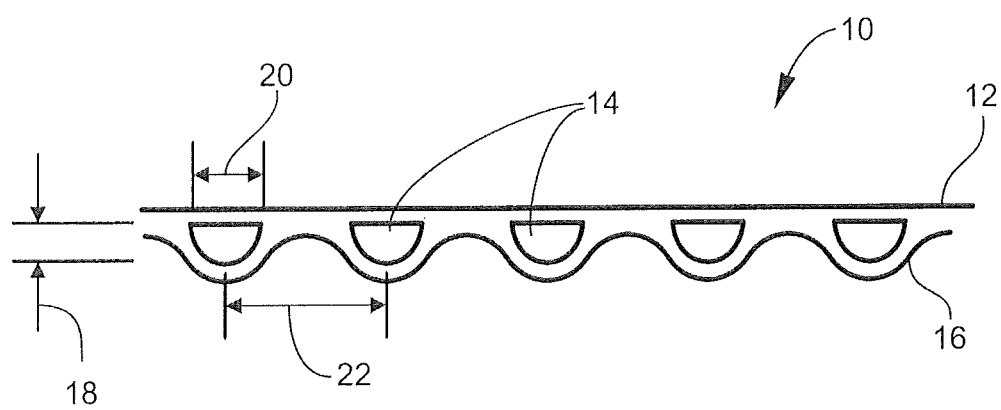
FIG. 1 is a schematic diagram illustrating a cross-sectional view of one embodiment of a system in accordance with the present invention.
Figure 2:
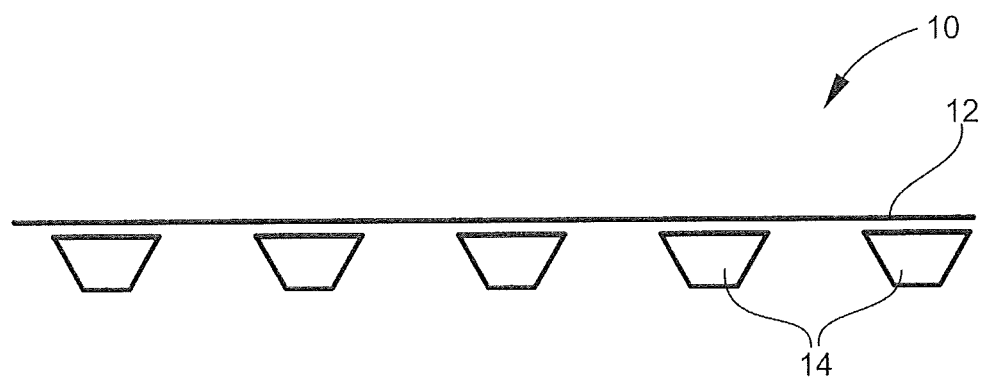
FIG. 2 is a schematic diagram illustrating a cross-sectional view of an alternative embodiment of a system in accordance with the present invention where the inner material has been omitted.
Figure 3:
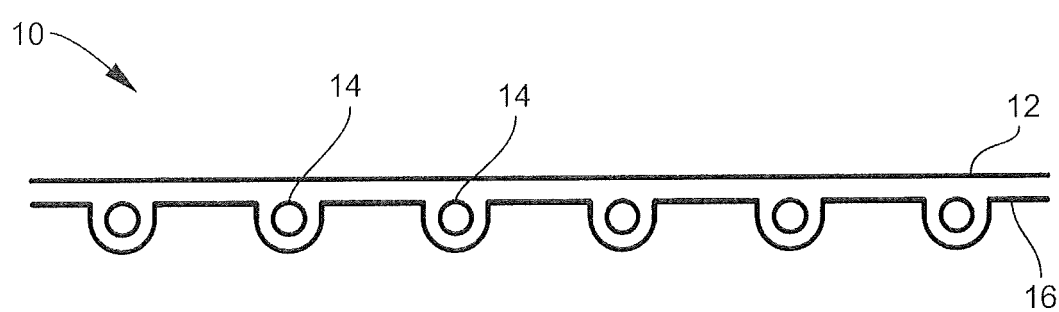
FIG. 3 is a schematic diagram illustrating a cross-sectional view of another alternative embodiment of a system in accordance with the present invention.
Figure 4:
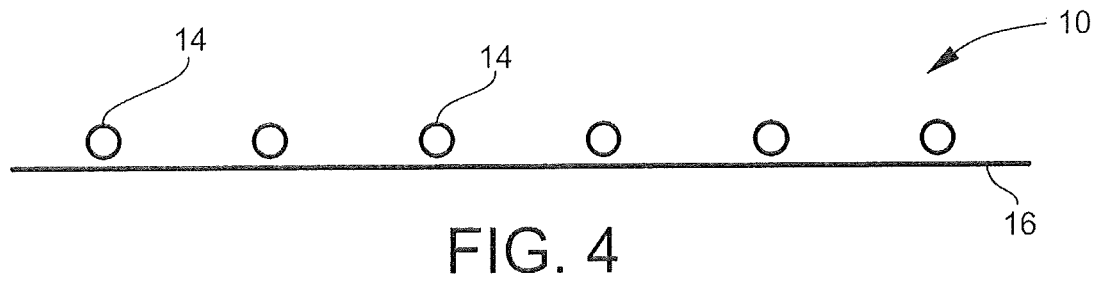
FIG. 4 is a schematic diagram illustrating a cross-sectional view of another alternative embodiment of a system in accordance with the present invention where the outer material has been omitted.
Figure 5:
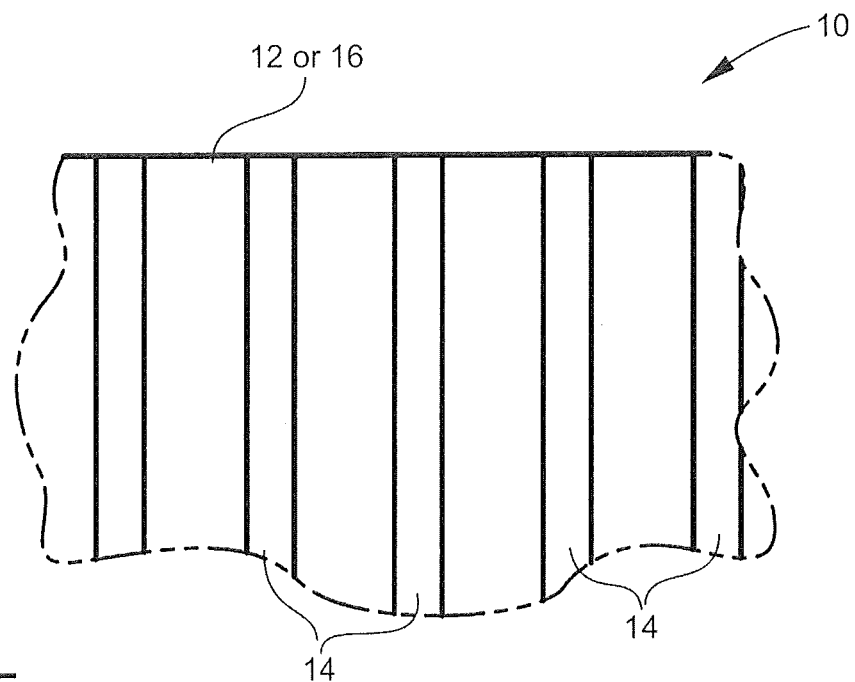
FIG. 5 is a schematic diagram illustrating a partial plan view of one embodiment of a system in accordance with the present invention.
Figure 6:
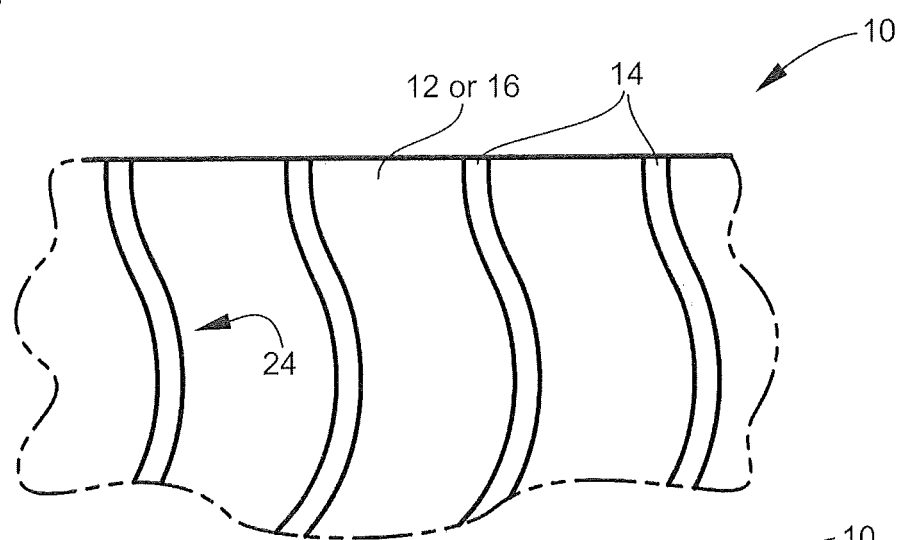
FIG. 6 is a schematic diagram illustrating a partial plan view of an alternative embodiment of a system in accordance with the present invention where the elements are not linear.
Figure 7:
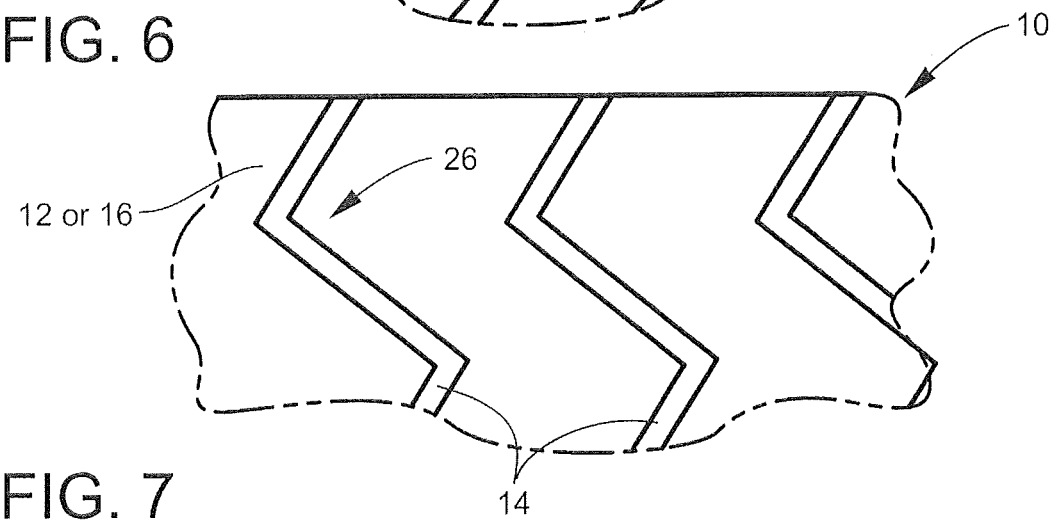
FIG. 7 is a schematic diagram illustrating a partial plan view of another alternative embodiment of a system in accordance with the present invention where the elements are not linear.
Figure 8:
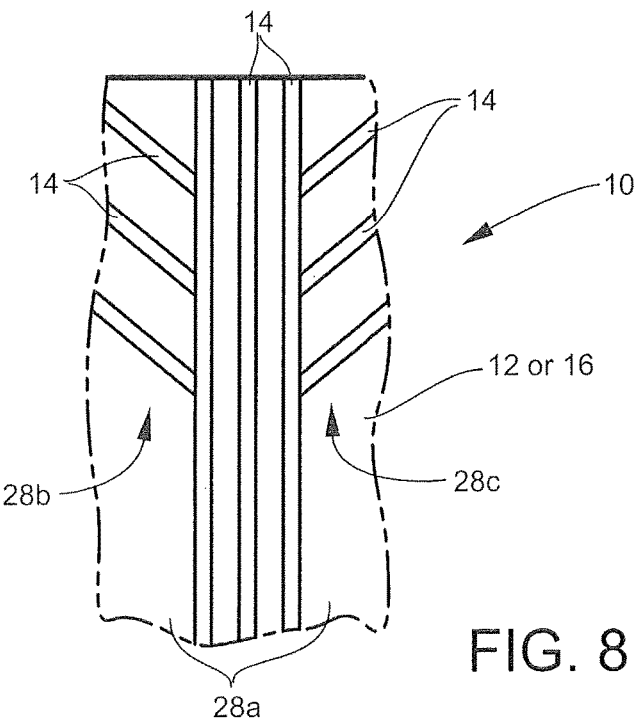
FIG. 8 is a schematic diagram illustrating a partial plan view of another alternative embodiment of a system in accordance with the present invention different sets of elements have different orientations.

It will be readily understood that the components of the present invention, as generally described and illustrated in the drawings herein, could be arranged and designed in a wide variety of different configurations. Thus, the following more detailed description of the embodiments of the system and method of the present invention, as represented in the drawings, is not intended to limit the scope of the invention, but is merely representative of various embodiments of the invention. The illustrated embodiments of the invention will be best understood by reference to the drawings, wherein like parts are designated by like numerals throughout.

Referring to FIGS. 1-4, in certain embodiments, a system 10 in accordance with the present invention may have a lower profile, conform more closely to the contours of a limb of patient or user, be lighter in weight, breathe better, and stretch better than traditional compression technology. Additionally, a system 10 in accordance with the present invention may augment or encourage lymphatic flow in a dual manner (i.e, by augmenting dermal lymphatic flow with a push-pull action and/or by achieving regional pressure gradients to improve lymph drainage).

In selected embodiments, a system 10 may be embodied or function as a compression garment or as a liner to a compression garment. In embodiments where the system 10 is embodied or functions as a liner, a compression wrap or garment of elastic or inelastic material may be applied over the system 10 (i.e., to urge the system 10 against the limb of a patient or user). Alternatively, the system 10 may be worn underneath a traditional compression sleeve (i.e., a circular or flat knit compression sleeve).

FIGS. 1-4 provide cross-sectional views of various embodiments of a system 10 in accordance with the present invention. In selected embodiments, a system 10 may include an outer material 12 (i.e., outer fabric, layer, or the like), a plurality of elements 14, and an inner material 16 (i.e., inner fabric, layer, or the like). In selected embodiments, an inner material 16 may abut or contact the skin of a patient or user of a system 10. Accordingly, an inner material 16 may be sueded for comfort or comprise a "techsheen" fabric to provide a silky feel. An inner material 16 may or may not contribute to compression applied to a user of the system 10. In certain embodiments, both outer and inner materials 12, 16 may have sufficient stretch between elements 14 to enable the corresponding system 10 to conform to the limb of the user and provide therapeutic compression.

Inner layer 16 and outer layer 12 materials may be the same or different fabric type and these layers may be knitted (e.g., Rochelle, Tricot, or another weave), woven, and/or non-woven elastomeric materials such as weffloc, powernet, techsheen, lockstitich, superlock, triskin, stretch satin, gentilisimo, circular knit compression fabric, or flat knit compression fabric. One or both inner and outer materials 16, 12 may consist of, or includes comprise hook and loop or similar touch fastener compatible materials.

In selected embodiments, an inner material 16 may be omitted. In such embodiments, an outer material 12 may be positioned exterior to one or more elements 14 and urge those elements 14 against a user or patient. Alternatively, an outer material 12 may be positioned exterior to one or more elements 14 and a compressive wrap or sleeve may be positioned exterior to the outer material 12. Accordingly, the compressive wrap or sleeve may urge the elements 14 against a user or patient.

In certain embodiments, an outer material 12 may be omitted. In such embodiments, an inner material 16 may be positioned interior to one or more elements 14 and hold those elements 14 in place with respect to a user or patient. Accordingly, a compressive wrap or sleeve may urge the elements 14 against a user or patient.

In selected embodiments, a system 10 in accordance with the present invention may be built into a compression garment. For example, a system 10 may be built or integrated into a sheet-based compression garment like the FarrowWrap 4000, or FarrowWrap Trim-to-Fit (TTF) or a banded compression garment like the FarrowWrap formed with overlapping bands that extend circumferentially around a limb of a patient or user. A system 10 may be built or integrated into compression garments that are substantially inelastic, elastic, or have limited linear stretch (e.g., shortstretch).

In the case of a short-stretch system 10 or a system 10 incorporated within a short-stretch garment, the fabric (e.g., the outer material 12, the inner material 16, or some other material) may be stretched until it reaches an abrupt, userappreciable end-stretch. This would inform the user when to quit pulling. Such an end stretch may be reached after an elongation of about 15 to about 100%. In preferred embodiments, the end stretch may be reached after an elongation of about 15 to about 40%, where the fabric achieves the therapeutic compression levels described below.

Compression levels applied by or through a system 10 in accordance with the present invention may fall into a typical American standard compression range of about 8-15 mmHg, about 15-20 mmHg, about 20-30 mmHg, about 30-40 mmHg, or even about 40-50 mmHg. In other embodiments, the compression levels may fall into the Raul standard, French standard, another compression range standard known in the art, or within a custom standard.

The elements 14 of a system 10 in accordance with the present invention may extend generally parallel to one another. Such elements 14 may be attached at certain intervals to the outer material 12, inner material 16, both. In selected embodiments, one or more elements 14 may comprise polyurethane foam, viscoelastic foam, spacer fabric, rubber, silicone, polymeric material, or the like. Accordingly, elements 14 in accordance with the present invention may be compressible or semi-compressible.

In selected embodiments, the density or distribution of elements 14 with respect to an outer or inner material 12, 16 may be substantially uniform throughout a system 10 or with respect to a patient or user. Alternatively, in certain areas, the density or distribution of elements 14 with respect to an outer or inner material 12, 16 may be greater than in other areas. For example, in selected embodiments, there may be a higher density of elements 14 (e.g., the spacing between elements 14 may be less) in areas of a system 10 that correspond to the shin, malleoli, or the like of the patient or user. In certain embodiments, there may be a higher density of elements 14 (e.g., the spacing between elements 14 may be less) in areas of a system 10 that correspond to a posterior calf area to improve the calf muscle pump.

Each element 14 in a system 10 may be sewn, ultrasonically welded, thermally bonded, glued, or otherwise secured to an outer material 12, inner material 16, both. When urged against a limb of a patient, elements 14 in accordance with the present invention may create areas of higher pressure. Area in between the elements 14 may be of lower pressure. Accordingly, the elements 14 may form channels that help direct lymph flow up the limb and reduce swelling.

When viewed in cross-section, one or more elements 14 may have a height 18 and width 20 and be spaced a selected distance 22 from one another. In selected embodiments, one or more elements 14 may have a height 18 in the range of about 0.2 cm to about 2.5 cm, a width 20 in the range of about 0.5 cm to about 3.0 cm, and spacing 22 (e.g., on center spacing or spacing from edge to edge) in the range of about 0.5 cm to about 4 cm.

In selected embodiments, one or more elements 14 of a system 10 in accordance with the present invention may have a trapezoidal or rectangular (e.g., square) cross section. These shapes may provide an element 14 with wide, relatively flat surfaces enabling or supporting good adhesion or bonding between the element 14 and the corresponding outer material 12, inner material 16, or both.

In other embodiments, one or more elements 14 of a system 10 in accordance with the present invention may have a circular, elliptical, or partially rounded (e.g., semi-circular) cross-section. For example, an element 14 may have a semi-circular cross-section where the flat side is oriented away from the patient or user and the rounded side is oriented toward the patient or user. Alternatively, an element 14 may have a circular or elliptical cross-section where one rounded side is oriented away from the patient or user and an opposite rounded side is oriented toward the patient or user.

Referring to FIGS. 5-8, elements 14 in accordance with the present invention may be entirely linear, generally linear, or non-linear along their respective lengths. For example, in certain embodiments, one or more elements 14 may extend substantially parallel to one another. Alternatively, one or more elements 14 of a system 10 may be slightly serpentine in appearance with regular or irregular curves 24, zig zags 26, or the like.

In selected embodiments, a system 10 may include elements 14 with different orientations or arrangements. For example, a system 10 may include one or more sets 28 of elements 14. The elements 14 of each set 28a, 28b, 28c may be generally parallel to or match or track one other. However, the elements 14 of one set 28a may be oriented differently than the elements 14 of one or more other sets 28b, 28c, Accordingly, in selected embodiments, the elements 14 of a system 10 may be oriented and positioned to direct or funnel fluid within the body of the patient or user toward regional lymph nodes of the affected limb or body area. At the regional lymph nodes, lymphatic vessels may drain fluid from the dermal surface area into deeper lymphatics.

Referring to FIGS. 9-12, in selected embodiments, a system 10 in accordance with the present invention may be formed of spacer fabric (e.g., a single layer of spacer fabric). The spacer fabric may comprise two layers of fabric and filaments spanning the two layers of fabric to create a three dimensional product. The spacer fabric may be several millimeters in height and semi-compressible. Additionally, the spacer fabric may have some elasticity and be suitable for providing compression to a patient or user.

In certain embodiments, the two layers of a spacer fabric may be or form the inner and outer materials 16, 12 of a system 10 in accordance with the present invention. Accordingly, in selected embodiments, one or both of the inner and outer materials 16, 12 of a spacer fabric may be elastic to at least some degree. The height created by a cross filament 30 spanning the two layers (i.e., the inner and outer materials 16, 12) may be varied to form elements 14. Accordingly, the elements 14, and the channels defined thereby, may be programmed into the design of the spacer fabric at time of manufacture. In selected embodiments, cross filaments 30 may be monofilaments or contain multiple fibers. The diameter and materials chosen for the cross filaments 30 may control the overall rigidity (i.e., spring constant or resistance to deflection) and height of the feature 14 produced thereby. In certain embodiments the distance between a highest point on an element 14 and an outer material 12 may be greater than about 0.2 cm or may be in the range of about 0.2 cm to about 1.5 cm. In one embodiment, the distance between a highest point on an element 14 and an outer material 12 may be with a range from about 0.3 cm to about 0.6 cm.

Figure 9:
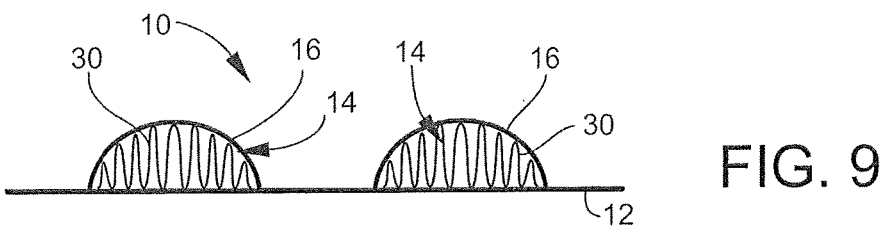
FIG. 9 is a schematic diagram illustrating a cross-sectional view of one embodiment of a system in accordance with the present invention formed of a spacer fabric where the inner material is intermittent.
Figure 10:
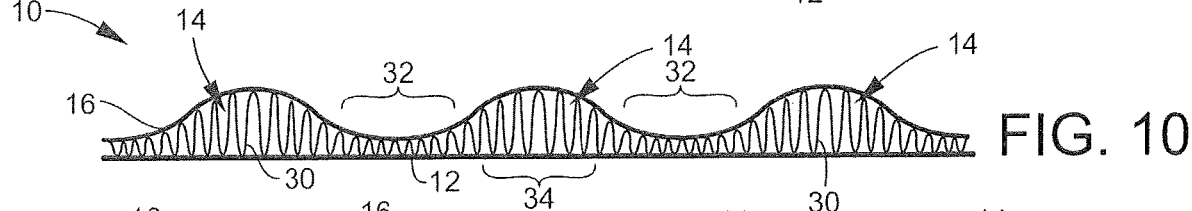
FIG. 10 is a schematic diagram illustrating a cross-sectional view of an alternative embodiment of a system in accordance with the present invention formed of a spacer fabric.
Figure 11:
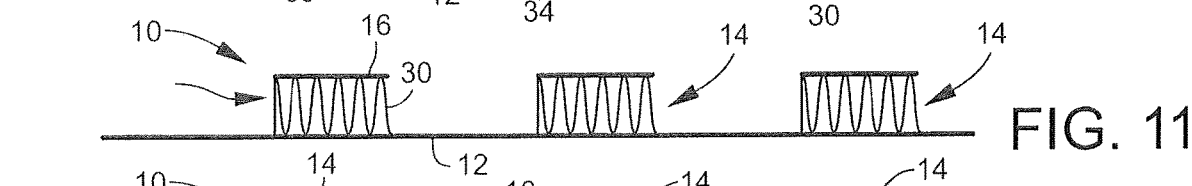
FIG. 11 is a schematic diagram illustrating a cross-sectional view of another embodiment of a system in accordance with the present invention formed of a spacer fabric where the inner material is intermittent.
Figure 12:
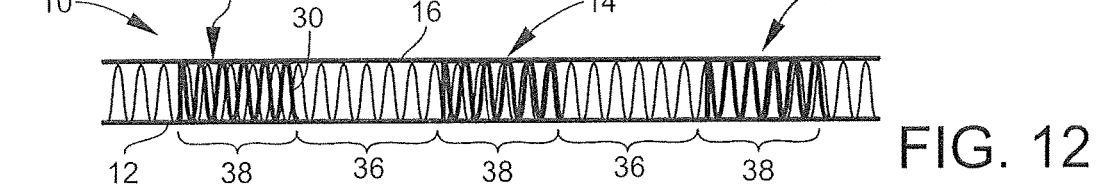
FIG. 12 is a schematic diagram illustrating a cross-sectional view of another alternative embodiment of a system in accordance with the present invention formed of a spacer fabric that has a substantially constant height.

In selected embodiments, a spacer fabric forming a system 10 in accordance with the present invention may include certain areas where only one of the layers (i.e., one of the outer or inner materials 12, 16) is presented and other areas where both layers (i.e., both the outer and inner materials 12, 16) are present and spanned by the cross filaments 30 to form an element 14. This intermittency may be accomplished more gradually as shown in FIG. 9 or more abruptly as shown in FIG. 11. In such embodiments, the areas where the two layers are present and spanned by the cross filaments 30 may correspond to or form elements 14.

Alternatively, both layers of a spacer fabric may be continuous, but the length of the cross filaments 30 may vary. For example, in certain regions 32, the cross filaments 10 may be relatively short. In other regions 34, the cross filaments 30 may be relatively long. The regions 34 where the cross filaments 30 are relatively long may correspond to or form elements 14. In selected embodiments, the longer regions 34 may be about 1.5 to about 5 times higher (i.e., thicker) than the shorter regions 32. In certain embodiments, the longer regions 34 may be about two to three times higher than the shorter regions 32. The weave, filament 30, filament pattern, or the like may be the same in both the longer and shorter regions 34, 32, Alternatively, the longer regions 34 may include or comprise a higher concentration of cross filaments 30.

In still other embodiments, both layers of a spacer fabric may be continuous, but the resistance of the cross filaments 30 to deflection or compression may vary. For example, in certain regions 36, the cross filaments 10 may be relatively thin, applied less densely, or both. In other regions 38, the cross filaments 30 may be relatively thick, applied more densely, or both. The regions 38 where the cross filaments 30 are relatively thick and/or more densely applied may correspond to or form elements 14. That is, those regions 38 may provide a greater resistance to deflection or compression and, as a result, provide areas of higher and lower compression to channel fluid in accordance with the present invention. This channeling may be more pronounced when compression is applied over the spacer fabric to urge the spacer fabric against the underlying tissue or limb of the patient or user.

Figure 13:
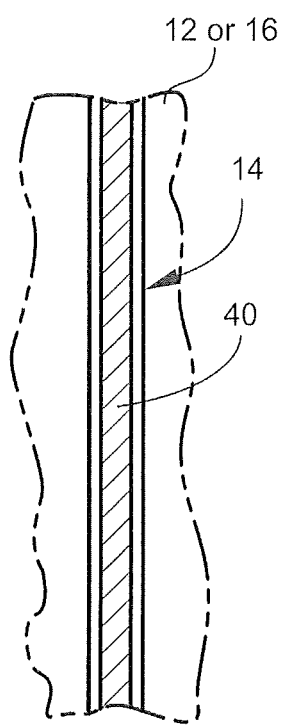
FIG. 13 is a schematic diagram illustrating a partial plan view of one embodiment of a system in accordance with the present invention where an element corresponds to or is tracked by a region supporting macro-gripping.
Figure 14:
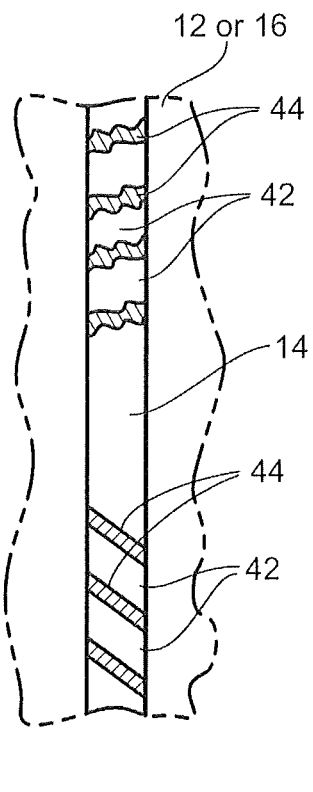
FIG. 14 is a schematic diagram illustrating a partial plan view of one embodiment of a system in accordance with the present invention where an element corresponds to or supports one or more regions providing micro-channeling and/or micro-gripping.
Figure 15:
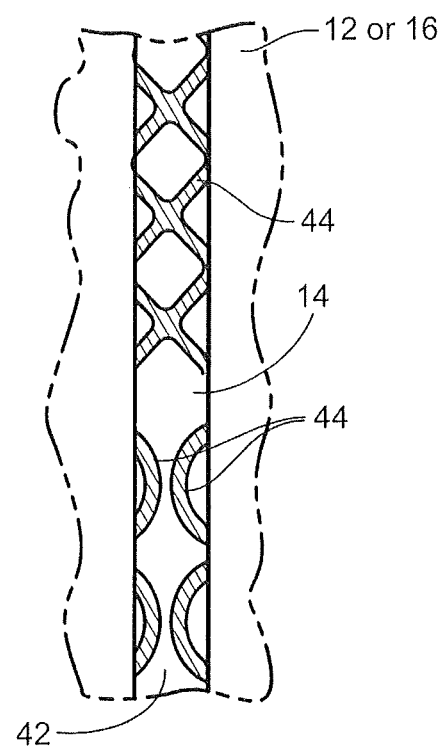
FIG. 15 is a schematic diagram illustrating a partial plan view of an alternative embodiment of a system in accordance with the present invention where an element corresponds to or supports one or more regions providing micro-channeling and/or micro-gripping.

Referring to FIG. 13, in selected embodiments, a system 10 in accordance with the present invention may provide macro-gripping. For example, a system 10 may include areas 40 having a higher coefficient of friction with respect to the skin of the patient. In certain embodiments, these areas 40 may correspond to and track one or more elements 14 of a system 10. Accordingly, areas of greater compression may be accompanied by better gripping of the skin of the patient or user. Thus, as a patient or user moves, certain areas 40 of a system 10 may tend to push or pull the skin of the patient or user more than other areas. This pushing and pulling may support or enhance dermal lymphatics.

In selected embodiments, elements in accordance with the present invention may enable or support micro-channeling, micro-gripping, or a combination thereof to support or enhance dermal lymphatics. For example, certain elements 14 may have micro-channels 42 or three-dimensional shapes molded, etched, or cut into their surface to further facilitate lymphatic flow and maximize the micro-pump action of lymphangion. Accordingly, micro-channels 42 may create, within the higher compression area produced by an element 14, tiny areas of relative higher and lower compression to help channel fluid.

Micro-gripping patterns 44 may create, within the higher compression area produced by an element 14, tiny areas 44 having a higher coefficient of friction with respect to the skin of the patient through a cutting or surface texturing or surface material. In selected embodiments, these areas 44 may correspond to and track one or more micro-channels 42 of a system 10. Thus, as a patient or user moves, certain areas 44 of a system 10 may tend to push or pull the skin of the patient or user more than other areas. This pushing and pulling may support or enhance dermal lymphatics.

Micro-channels 42, micro-gripping patterns 44, or combinations thereof may be on the elements 14 themselves or may be knitted, woven, deposited, or otherwise transferred onto the surface of an inner material 16. In selected embodiments, silicone (e.g., a bead of silicone) may be deposited on an element 14 or inner material 16 to create a micro-channel 42 (or portion thereof), micro-gripping pattern 44, or a combination thereof.

Figure 16:
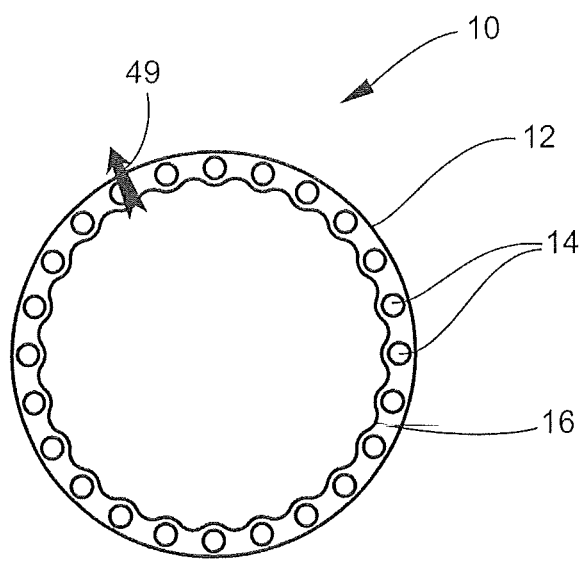
FIG. 16 is a schematic diagram illustrating a cross-sectional view of one embodiment of a system in accordance with the present invention formed into a tube to encircle a limb of a patient or user.
Figure 17A:
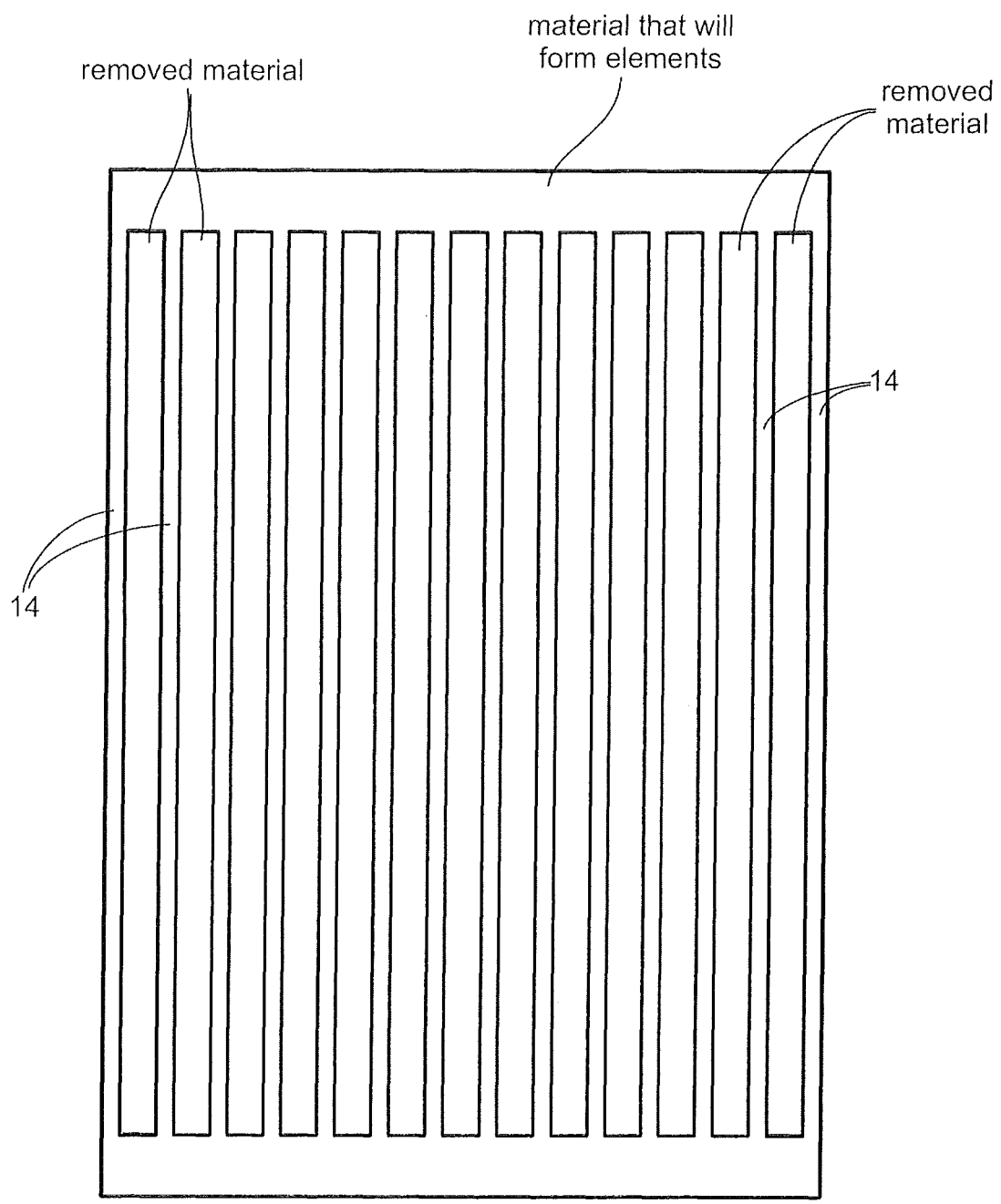
FIG. 17a is a schematic diagram illustrating a plan view of a sheet of material that may be cut to form multiple elements and hold those elements in place during an assembly process.
Figure 17B:
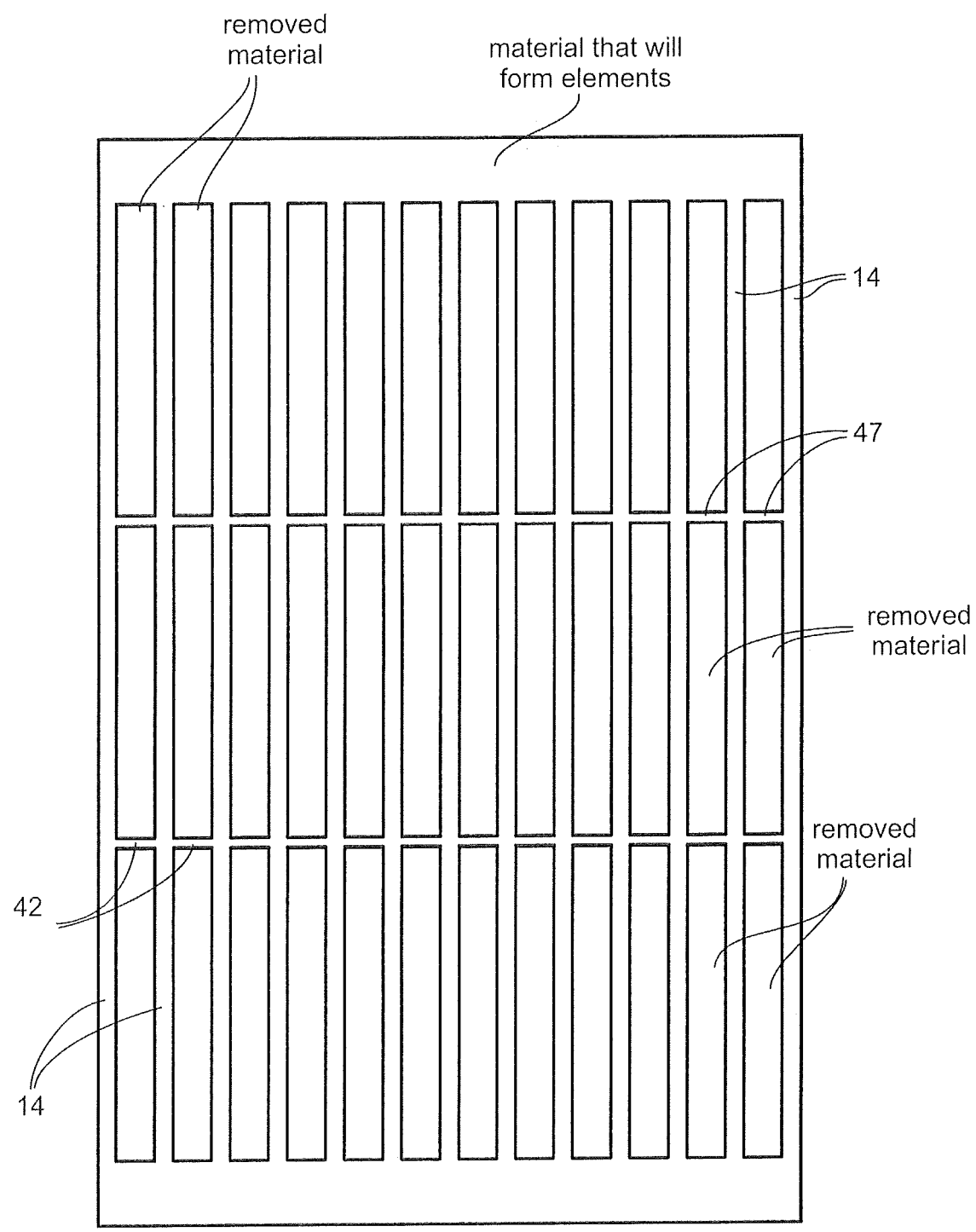
FIG. 17b is a schematic diagram illustrating a plan view of a sheet of material that may be cut to form multiple elements with bridges.
Figure 18:
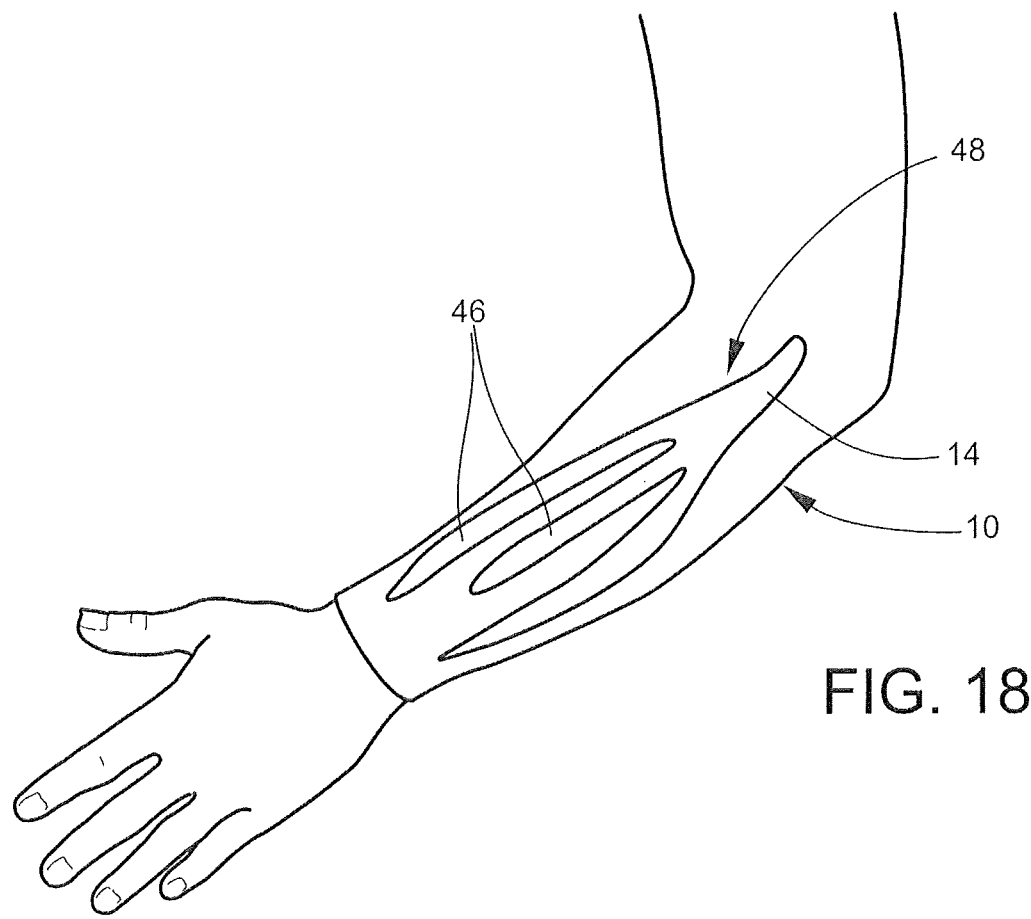
FIG. 18 is a schematic diagram illustrating one embodiment of a system applied to an arm, the system including an element that is anatomical in accordance with the present invention.
Figure 19:
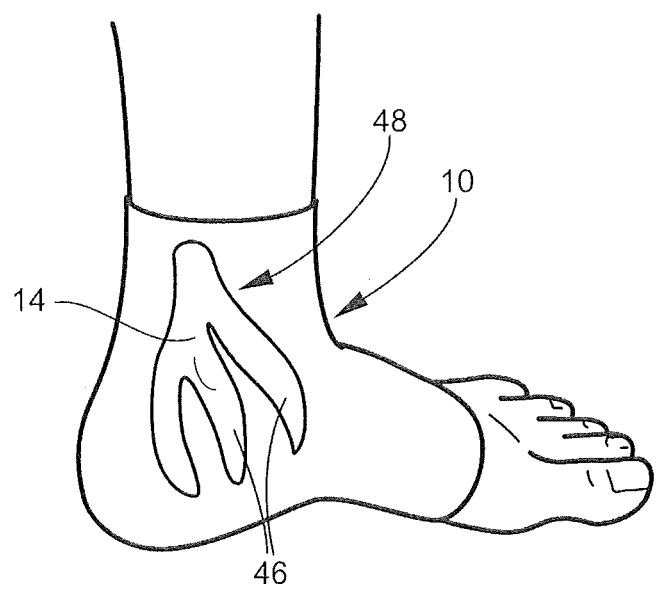
FIG. 19 is a schematic diagram illustrating one embodiment of a system applied to a foot, the system including an element that is anatomical in accordance with the present invention and may help reduce ankle swelling and speed recovery from sports injuries.
Figure 20:
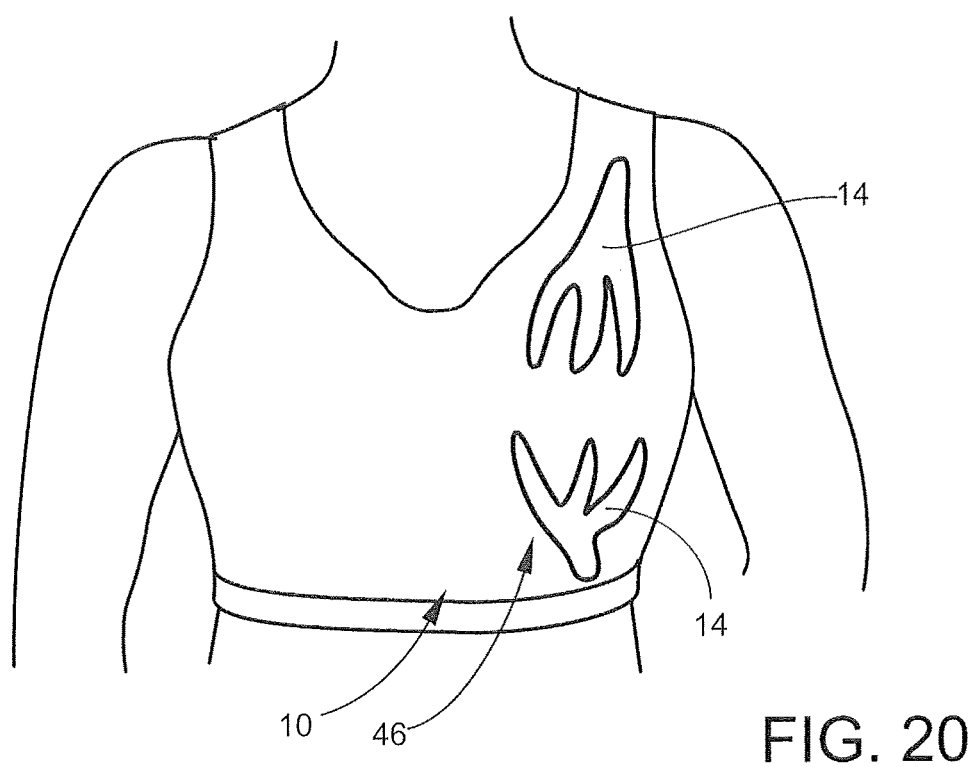
Figure 21:
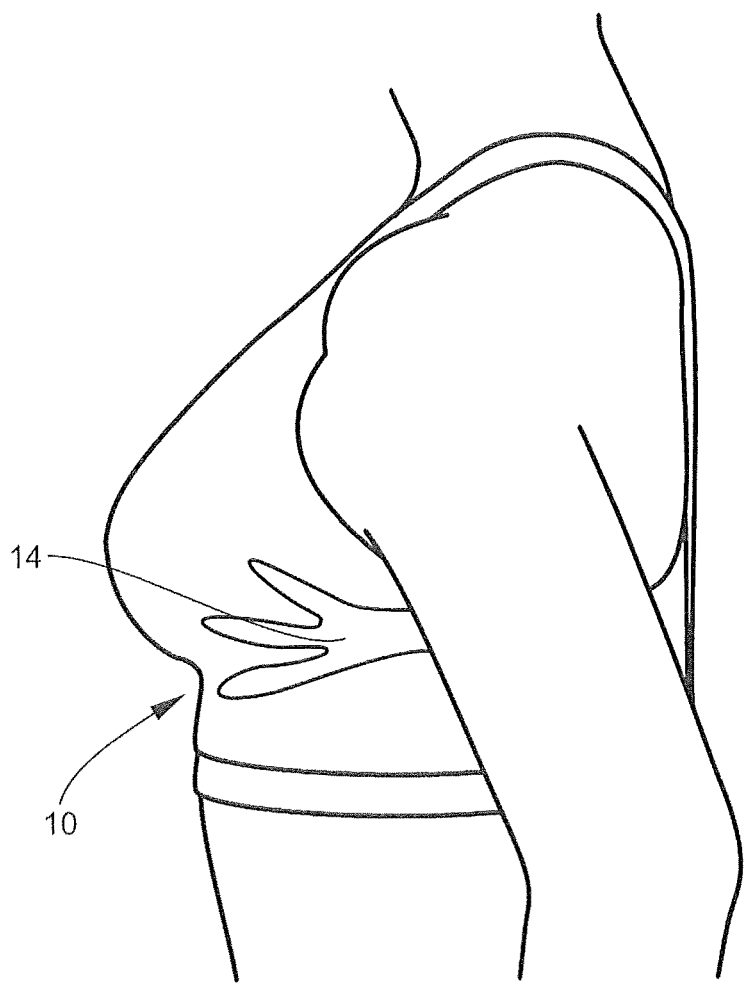
Figure 22:
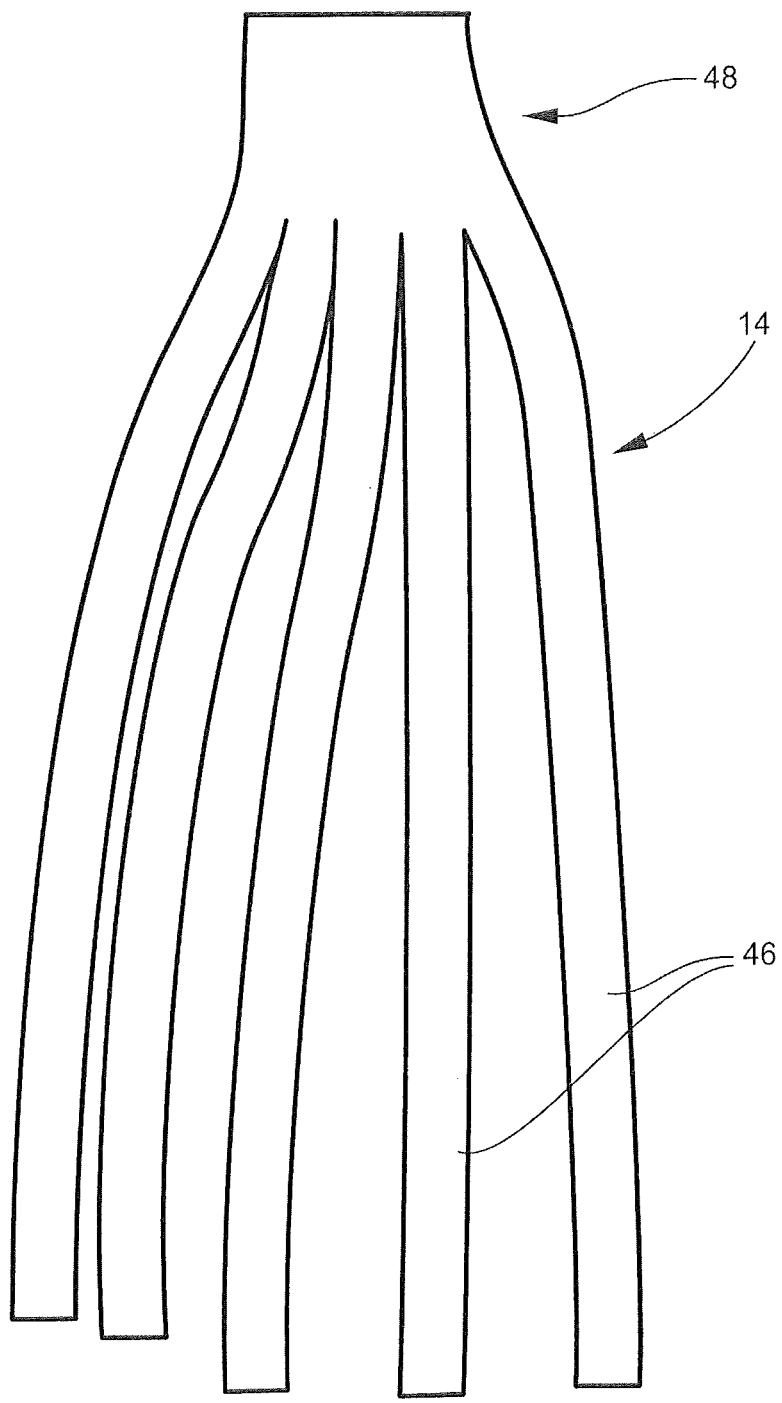
FIG. 22 is a schematic diagram illustrating a plan view of one embodiment of an element that is anatomical in accordance with the present invention.
Figure 23:
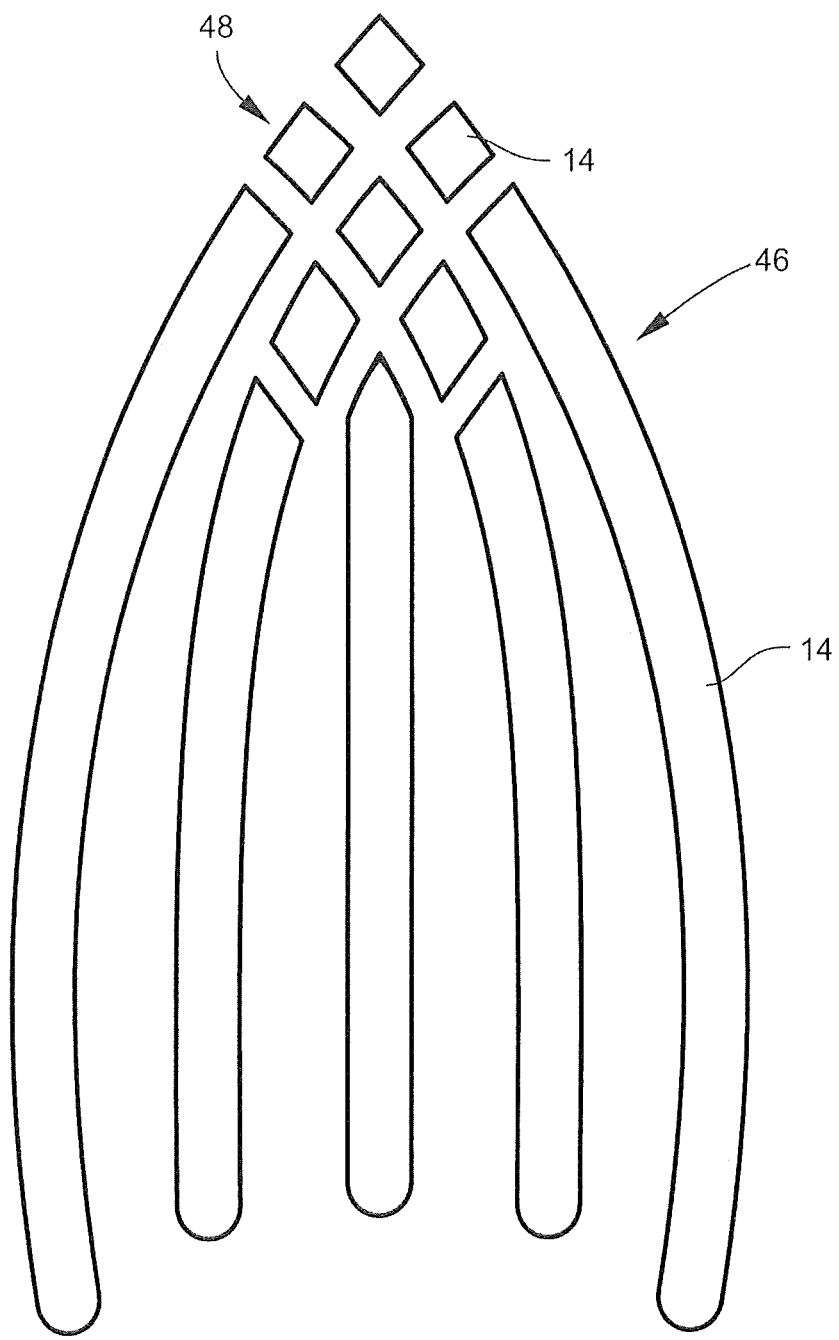
FIG. 23 is a schematic diagram illustrating a plan view of an alternative embodiment of an element that is anatomical in accordance with the present invention.
Figure 24:
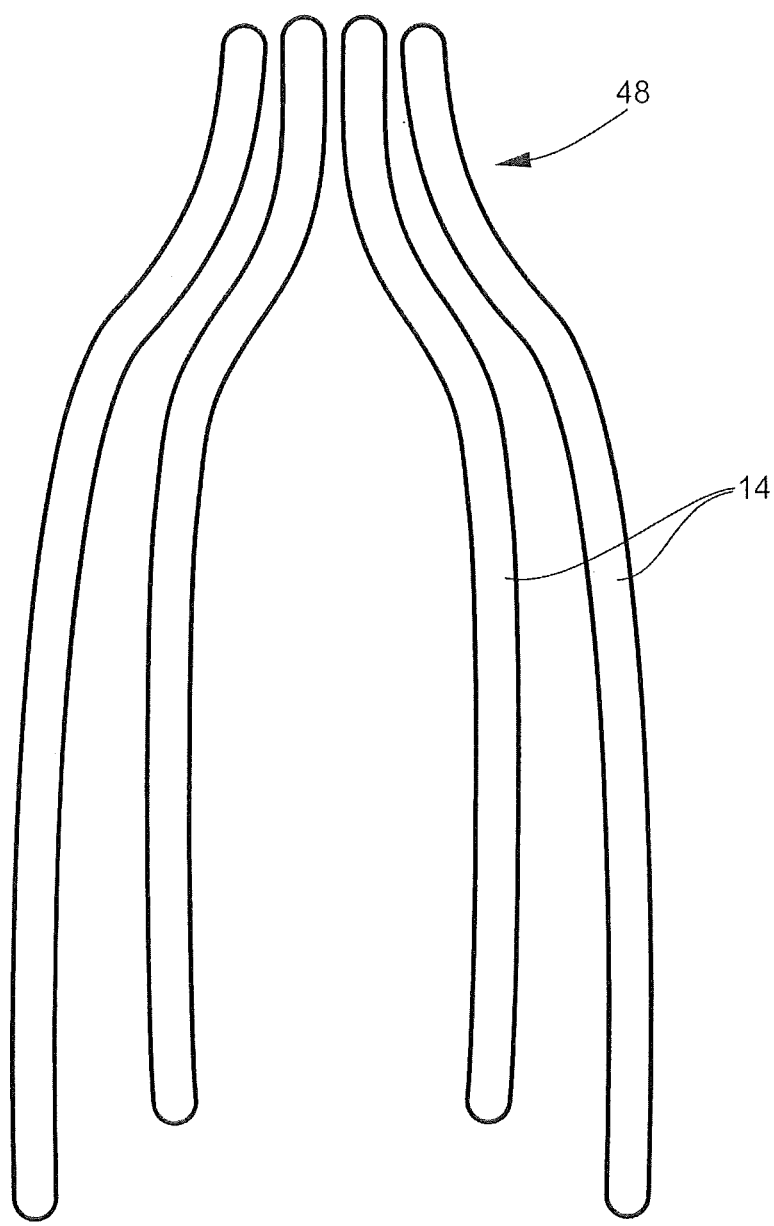
FIG. 24 is a schematic diagram illustrating a plan view of another alternative embodiment of an element that is anatomical in accordance with the present invention, the element includes multiple projections that converge, but do not touch.

Referring to FIGS. 16, 17a, and 17b, in selected embodiments, a method of manufacturing or assembling a system 10 in accordance with the present invention may include holding one or more elements 14 in place and sewing, thermally bonding, gluing, ultrasonically welding, adhering using a heat laminate adhesive (HLA), or the like those elements 14 to an outer material 12, inner material 16, both.

For example, in a first step, the material that will form the elements 14 (e.g., foam, spacer fabric, or the like) may be coated with a heat laminate adhesive (HLA) on both sides (or only one side if one of the outer material 12 or inner material 16 is to be omitted). After the HLA is applied, the material may be cut into the proper shape (e.g., using a robotic cutting table, jig and press). In selected embodiments, such cutting may comprise removing the unwanted material from a center portion and leaving the ends of the elements 14 connected to maintain their proper orientation and spacing with respect to one another (see e.g., FIG. 17a). Alternatively, the material that will form the elements 14 may comprise separate sections that may be placed within a jig that will define and maintain a proper orientation and spacing for the elements 14.

In certain embodiments, one or more bridges 47 may be formed in the material that will form the elements 14. The bridges 47 may hold the elements 14 connected and maintain their proper orientation and spacing with respect to one another during manufacture and/or use of the system 10. In selected embodiments, one or more bridges 47 may be have a height lower than that of the adjacent elements 14.

Bridges 47 may be spaced irregularly or periodically, and may allow for both radial and axial air flow through the system 10, resulting in a light weight and breathable product. In certain embodiments, the number of bridges 47 and width of the bridges 47 may an affect overall compression profile of the system 10. For instance, using higher density of bridges 47 distally in limb or wider bridges 47 distally in the limb may create more compression distally in the system 10.

Similarly, by placing more bridges 47 to a problem swelling area or lobule that swells, there may be an increase ability to control swelling to that problem area. Similarly, a higher density of bridges 47 or increase bridge 47 widths may be used over the calf area to create a progressive compression profile (e.g., more compression to the calf than to the ankle). Thus, a custom compression profile can be chosen for the garment by alternating the number of bridges 47, the width of each bridge 47, and the relative location of one bridge 47 relative to another bridge 47.

In such a design, the surface area without elements may be about 30% to about 75% of the total surface area of the garment. The elements would be mostly symmetrically and/or uniformly distributed, but in some embodiments there may be wider or anatomically shaped elements over bony areas to provide more therapeutic padding, such as over the anterior tibialis tendon (anterior ankle area), malleoli, and shin areas in the case of a lower leg garment.

In selected embodiments, there may be larger bridges 47 or areas of solid material 14 over the posterior calf area in order to reduce overall stretch of the system 10 and maximize the calf muscle pump. Thus, while the elements 14 would be mostly symmetrical and/or uniformly distributed and rather sparse, areas with extra elements 14 may be used to pad the system 10 for maximal safety and comfort to the patient, or to increase compressive force when donned by the elements 14 limiting the stretch of that section of the system 10. Thus, but controlling the density or distribution of the elements 14 about a limb circumference, the stretch of the system 10 over that area and thus the compression level of the system over that area of the patient may be increased or decreased.

Next, a fabric layer (one of the outer or inner materials 12, 16) may be laid on top of the material that will form the elements 14. An iron or a heat press may then bond the fabric to the elements 14. If another fabric layer (the other of the outer or inner materials 12, 16) is to be applied, the material that will form the elements may be flipped over and a second layer of fabric may be applied to the opposite side. The resulting structure may then be cut into the correct shape for a particular a limb or body portion. This may included cutting off the ends of the elements 14 that were left connected to maintain a proper orientation and spacing of the elements 14 during assembly. At this point, the structure may be considered to be a system 10 in accordance with the present invention.

In selected embodiments, system 10 may be cut to fit a portion of a limb of a patient or user. Accordingly, after the system 10 is cut to the proper perimeter, is may be formed into a tube and secured in that shape. Alternatively, to make it easier to put on, a patient or user may wrap the system 10 around a limb in a donning process.

In certain embodiments, other manufacturing methods may be used. For example, spacer fabric may be manufactured on circular machines (i.e., machines that can "knit" a tube of the like). Accordingly, in selected embodiments, a spacer fabric may be manufactured in a continuous circle with the appropriate features of a system 10 in accordance with the present invention. Thus, the spacer fabric may need only to be trimmed and finished at the top and bottom to complete the system.

In certain embodiments, water vapor and other gas may be free to pass in a radial direction 49 through the inner and/or outer materials 16, 12 in the areas between the elements 14. Alternatively, or in addition thereto, water vapor and other gas may be free to pass in an axial direction 49 (i.e., parallel to the elements 14) through the system 10 in the spaces between elements 14. This axial flow may improve breathability in situations where a system 10 in accordance with the present invention is positioned below or interior to a compression garment that restricts the flow of gas in the radial direction 49. Accordingly, a system 10 in accordance with the present invention may breathe well.

This breathability may increase comfort, decrease weight and bulk, decrease moisture next to the skin, and use less material than a bulky garment with lots of foam. By using higher or lower compression fabric for one or both of the outer and inner materials 12, 16, a system 10 may function well as a liner or as a compression garment itself. Accordingly, in selected embodiments, the outer and/or inner materials 12, 16 may provide all or substantially all of the compression needed or used on a limb of a patient or user. Additionally, having a good amount of stretch in the outer and/or inner materials 12, 16 may maximize garment conformability and comfort.

In selected embodiments, a significant portion of a limb circumference covered by a system 10 in accordance with the present invention may be free to breath in the radial and/or axial directions. Areas that are free to breathe or breathable may be areas that are not being directly compressed beneath an element 14.

In certain embodiments, about 30 to about 50 percent of a circumference of an unstretched system 10 may be without compressive elements 14 and thus with maximal breathability. When a system 10 is applied to a patient or user, the outer and/or inner materials 12, 16 between the elements 14 may stretch more than the portions of those materials 12, 16 secured to the elements 14. Accordingly, when a system 10 is applied to a patient or user, about 45 to about 75 percent surface area of a circumference of a stretched system 10 may be without compressive elements 14 and thus one to two layers to maximal breathability.

In other embodiments, about 50 percent or greater of a circumference of an unstretched system 10 may be without compressible elements 14. Accordingly, when such a system 10 is applied to a patient or user, about 55 to about 95 percent surface area of a circumference of a stretched system 10 may be without compressive elements 14 with just one to two layers.

Referring to FIGS. 18-29, in selected embodiments, one or more elements 14 in accordance with the present invention may be anatomical. This means that a single element 14 or a collection 46 of elements 14 may be shaped and/or positioned so as to conduct or channel fluid to or away from specific anatomical features (e.g., lymph nodes or other features of a lymphatic system) of a patient or user.

In selected embodiments, a single element 14 that is anatomical may include a plurality of projections or fingers 18 that converge, gather, or the like at a point of convergence 50. A collection 46 of elements 14 that are anatomical may include a plurality of elements 14 that collectively converge, gather, or channel fluid toward a point of convergence 50. In selected embodiments, a collection 46 of elements 14 that are anatomical may be more flexible than a single element 14 that is anatomical.

Accordingly, such a collection 46 may better conform to the shape of the patient or user and channel lymph flow toward or away from the area 48 where the finger-like projections converge.

In certain embodiments, the curves of the finger-like projections 46 or of the discreet elements 14 may extend parallel each other. Alternatively they may be shaped and positioned to optimize flow around a joint or body area or to maximize surface area drained. In selected embodiments, the curvature may be chosen to maximize body range of motion without hampering comfort or movement.

In various figures, certain elements 14 within a collection 46 are shown in diamond shape. However, elements 14 having other shapes may be used in a collection 46. For example, elements 14 that are square, rectangular, circular, triangular, or the like may also be used.

Figure 29:
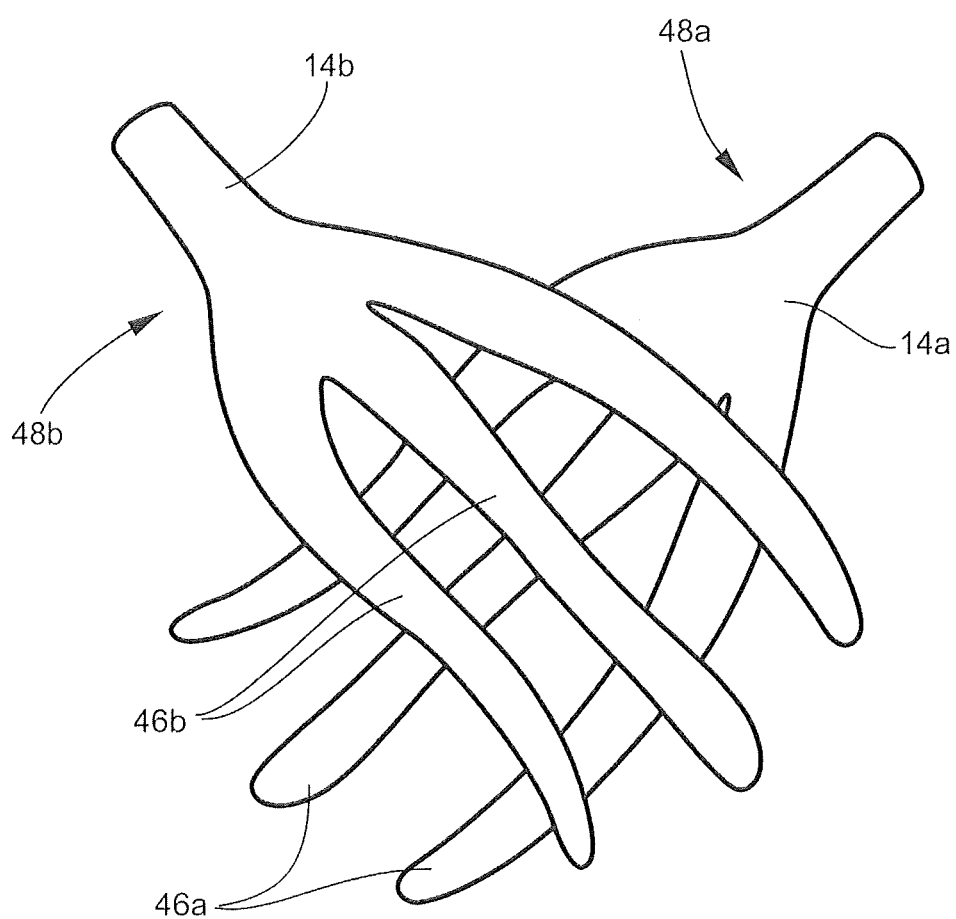
FIG. 29 is a schematic diagram illustrating a plan view of two elements that are anatomical in accordance with the present invention that at least partially overlap one another.

In selected embodiments, overlapping elements that are anatomical as shown in FIG. 29 may be applied to a shoulder of a patient or user by a compression shirt. Such an arrangement may help support the shoulder, reduce swelling, and/or improve lymphatic flow to the shoulder area.

The present invention may be embodied in other specific forms without departing from its spirit or essential characteristics. The described embodiments are to be considered in all respects only as illustrative, and not restrictive. All changes which come within the meaning and range of equivalency of the described embodiments are to be embraced within their scope.

What is claimed is:

1. A medical garment for channeling edema from a body region, the garment comprising linear elements, bridge areas, and at least one fabric layer, such that the surface area of the fabric layer increases after donning more than the surface area over the elements; and the surface area without elements or bridges is greater than 40% of the total surface area after donning.

2. The garment of claim 1, wherein the total garment surface area without compressive elements and with only one or two fabric layers is greater than 40% of the total surface area of the limb prior to donning, and wherein the relative percentage of surface area without compressive elements and with only one or two fabric layers increases after donning by at least 10%.

3. The garment of claim 2, wherein the relative percentage of surface area without compressive elements and with only the one or two fabric layers increases from about 50% to about 60% or more after donning to an appropriately sized limb.

4. The garment of claim 1, wherein the surface area without elements is greater than 50% of the total surface area after donning.

5. The garment of claim 1, wherein the surface area without elements is greater than 60% of the total surface area after donning.

6. The garment of claim 1, wherein the garment applies a therapeutic compression to the limb area in addition to channeling.

7. The garment of claim 1, wherein the compression range lies within one of 15-20 mmHg, 20-30 mmHg, 30-40 mmHg, or 40-50 mmHg in the distal area of the limb, after garment is properly sized and fitted to the limb.

8. A medical garment comprising:
an outer compression fabric, and
at least one inner semicompressible element secured to the outer compression fabric configured to urged against a limb of a patient by the outer compression fabric, the at least one inner semicompressible element having multiple fingers configured to project over the limb of the patient and to regionally direct edema out of the limb:
the at least one semicompressible element being made of at least one of foam, spacer fabric, polymer, and silicone.

9. The medical garment of claim 8, wherein the at least one inner semicompressible element is permanently bonded to the outer compression fabric.

* * * * *